(12) United States Patent
Pflanz

(10) Patent No.: US 9,404,075 B2
(45) Date of Patent: Aug. 2, 2016

(54) DEVICE AND METHOD FOR TREATING A FILTRATION MEDIUM

(75) Inventor: Karl Pflanz, Gleichen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 872 days.

(21) Appl. No.: 13/508,768

(22) PCT Filed: Oct. 20, 2010

(86) PCT No.: PCT/EP2010/006416
§ 371 (c)(1),
(2), (4) Date: May 9, 2012

(87) PCT Pub. No.: WO2011/057707
PCT Pub. Date: May 19, 2011

(65) Prior Publication Data
US 2012/0248022 A1    Oct. 4, 2012

(30) Foreign Application Priority Data

Nov. 12, 2009  (DE) .......................... 10 2009 052 671

(51) Int. Cl.
| | |
|---|---|
| *G01N 1/00* | (2006.01) |
| *B01L 3/00* | (2006.01) |
| *B01D 35/16* | (2006.01) |
| *B23P 17/04* | (2006.01) |

(Continued)

(52) U.S. Cl.
CPC .............. *C12M 47/02* (2013.01); *B01L 3/5635* (2013.01); *G01N 1/4077* (2013.01); *B01L 3/5021* (2013.01); *B01L 2300/0681* (2013.01); *Y10T 29/49826* (2015.01)

(58) Field of Classification Search
CPC .................... G01N 1/4077; G01N 2001/4088; B01L 3/5635; B01L 3/5021; B01L 2300/0681; C12M 47/02; C12M 1/123; C12M 3/062; Y10T 436/25375
See application file for complete search history.

(56) References Cited

U.S. PATENT DOCUMENTS

| | | | | |
|---|---|---|---|---|
| 4,938,389 | A | * | 7/1990 | Rossi et al. ............... 222/189.08 |
| 5,112,488 | A | * | 5/1992 | Lemonnier ............ B01D 29/05 210/541 |
| 5,471,994 | A | | 12/1995 | Guirguis |

(Continued)

FOREIGN PATENT DOCUMENTS

| | | |
|---|---|---|
| DE | 694 04 659 | 11/1997 |
| DE | 100 54 632 | 5/2002 |

(Continued)

OTHER PUBLICATIONS

English translation of the International Preliminary Report on Patentability.

*Primary Examiner* — Christopher A Hixson
(74) *Attorney, Agent, or Firm* — Gerald E. Hespos; Michael J. Porco; Matthew T. Hespos

(57) ABSTRACT

A device for processing a porous filtration medium has a holding part that can be mounted on a lower part with the porous filtration medium. An outer wall of the holding part can be positioned outside a surface, of the filtration medium, and a fixing edge arranged in the holding part can be positioned on an edge of the filtration medium. The holding part has a filtration support which, on its side facing away from the filtration medium, is connected to an outlet for reverse flushing.

10 Claims, 7 Drawing Sheets

(51) Int. Cl.
    *C12M 1/00* (2006.01)
    *G01N 1/40* (2006.01)

(56) References Cited

U.S. PATENT DOCUMENTS

| | | | |
|---|---|---|---|
| 5,868,928 A * | 2/1999 | Bradley | 210/257.2 |
| 5,905,038 A * | 5/1999 | Parton | 435/287.6 |
| 5,976,824 A | 11/1999 | Gordon | |
| 2010/0028933 A1 | 2/2010 | Pflanz | |

FOREIGN PATENT DOCUMENTS

| | | |
|---|---|---|
| DE | 20 2004 005 694 | 8/2004 |
| DE | 699 32 901 | 3/2007 |
| DE | 10 2008 005 968 | 9/2008 |
| EP | 0 155 003 | 9/1985 |
| EP | 0 239 058 | 9/1987 |
| EP | 0 703 976 | 7/1997 |
| EP | 1 566 209 | 8/2005 |
| EP | 0 987 034 | 8/2006 |
| EP | 1 862 535 | 12/2007 |

\* cited by examiner

DEVICE AND METHOD FOR TREATING A FILTRATION MEDIUM

BACKGROUND OF THE INVENTION

1. Field of the Invention

The invention relates to a device for processing a porous filtration medium, having a holding part which can be mounted on a lower part, wherein an outer wall of the holding part can be positioned outside a surface, which can be used for filtration, of the filtration medium, and a fixing edge which is arranged in the holding part can be positioned on an edge of the filtration medium.

The invention also relates to a method for processing a porous filtration medium, in which method a holding part of a device is mounted on the filtration medium which is arranged in a lower part of a filtration device and which is exposed to a liquid sample, wherein a fixing edge which is arranged in the holding part is connected to an edge of the filtration medium and is raised, together with the filtration medium connected thereto, from the lower part.

2. Description of the Related Art

In the field of the analysis of liquids and gases, various processing methods have become established which use porous media such as filters and diaphragms. For example, the filtration method has become established for the depletion and concentration of dissolved or particulate components. Said concentration is usually necessary because the concentrations of the impurities are too low to carry out direct evaluations. The filtration methods serve as a preliminary stage for further analytical methods, such as optical evaluations, and also for further physical and chemical reactions for signal enhancement.

For newer, more sensitive analysis methods such as PCR ("Polymerase Chain Reaction") or mass spectrometry analysis, only very small sample volumes can be used. To be able to filter the in many cases typical sample volumes of more than 100 ml for the purpose of concentration, use is typically made of filtration diaphragms of 47 mm or 25 mm diameter. Even after the filtration, when the components or particles are present in concentrated form on the filtration diaphragm, the particles bound to the diaphragm cannot be supplied directly for analysis owing to the diaphragm size. It is necessary to transfer the retained components into a sample volume. If the sensitivity of the methods is to be fully utilized, said volumes must be as small as possible. Volumes of less than 1 ml, preferably 100 µl to 1 µl, are desirable, because, for example for PCR analysis, use is typically made of volumes of 20 µl to 1 µl, and the corresponding unused sample residual quantities come at the expense of sensitivity.

DE 10 2008 005 968 A1 discloses a nutrient medium unit and a method for receiving a filter from a filtration device. Here, the nutrient medium unit is composed of a cover or a holding part, which forms the actual transfer unit, and of a lower part which is filled with nutrient medium. Here, the upper part, which is formed as a holding part, has a fixing edge which, for the removal of the filtration medium from the filtration or processing device, can be connected to an edge of the filter by means of an adhesive bond.

DE 10 2008 005 968 A1 furthermore discloses a method for the microbiological examination of liquid samples, in which a cover or a holding part of a nutrient medium unit is mounted by way of a fixing edge on a filter which is arranged in a lower part of a filter or processing device and which is formed as a diaphragm filter. Here, the fixing edge of the holding part is connected to an edge of the filter by means of an adhesion layer.

The holding part is subsequently raised together with the filter from a filter support of the lower part of the filter device, and placed on a surface of a nutrient medium arranged in a lower part of a nutrient medium unit, wherein the cover or the holding part covers the shell-shaped lower part.

A disadvantage of the known filtration units and of the corresponding methods which have proven themselves for classic microbiological diaphragm applications, and which involve merely the removal of particles or, in the field of microbiology, the visual evaluation of colonies which have formed, is however that, after the filtration, the retained particles or the components thereof can no longer be removed from the diaphragm by flushing in such a way as to form highly concentrated suspensions.

Said disadvantages are of significance in particular in applications which do not correspond to the classic growth of retained germs on agar, but which rather use the modern molecular-biological marking and detection methods, regardless of whether these methods require pre-incubation or are examined directly by marking or enhancement methods.

DE 20 2004 005 694 U1 discloses an apparatus system for liquid testing, which apparatus system has, on a frame, a suction connecting piece to which is fastened, via an adapter, a filter bracket with a filtration diaphragm or a filtration medium, wherein a removable funnel is situated on the filter bracket. After a filtration process, the funnel is removed, and a DNA binding column is inserted, for further testing, between the suction connecting piece and adapter.

It is a disadvantage here that it is not possible for a universal filtration device or processing device to be used. It is also a disadvantage that, during the individual manipulations, there is the risk of contamination. It is also a disadvantage that reverse flushing of the filtration medium is not possible.

EP 1 566 209 A1 discloses a device and a method for vacuum-assisted affinity chromatography.

Here, too, a special device is required in which, furthermore, different exchangeable parts yield the risk of cross-contamination. In said device, too, as in the other devices, reversible flushing is not easily possible without removing the filtration medium.

It is therefore an object of the present invention to provide a device and a method with which it is possible for a porous filtration medium to be inserted in a simple and cheap manner, without further technical aids, into a further processing station in which, by means of the reverse filtration of a very small quantity of liquid, a large amount of the retained components can be transferred, in highly concentrated form, into a small volume.

SUMMARY OF THE INVENTION

The object with regard to the device is achieved in that the holding part has a filtration support which, on its side facing away from the filtration medium, is connected to an outlet for reverse flushing.

It is preferable here for that side of the filtration support which faces toward the filtration medium to face toward the retentate side of the filtration medium.

As a result of the arrangement of a filtration support in the holding part above the filtration medium, which filtration support is connected to an outlet, it is possible for the device or the holding part to be inserted upside down into a further processing station and for reverse flushing to be carried out without the filtration medium having to be removed from the holding part. The filtration medium is preferably disk-shaped and may be a porous diaphragm or some other suitable filter.

The device may form a separate filtration device or may be at least part of a separate filtration device. Here, the lower part and the holding part may be formed as disposable articles. It is also possible for the device as a whole to be formed as a disposable article or formed from disposable articles.

The lower part may however also be part of a first filtration device from which, with the holding part, the filtration medium is removed.

In one preferred embodiment of the invention, a detachable collecting vessel is connected to the outlet of the holding part. Since the outlet is already connected to a collecting vessel, the particulate components can be flushed out of the filtration medium and collected directly in the collecting vessel, without the need for an additional manipulation with the risk of contamination.

In a further preferred embodiment of the invention, the fixing edge of the holding part can be connected to the edge of the filtration medium by means of an adhesive bond. Here, the fixing edge of the holding part or the edge of the filtration medium has an adhesion layer composed of a suitable adhesive. By means of the adhesion layer, the disk-shaped filtration medium adheres to the holding part and can be easily removed from the processing device and processed further. It is however basically also possible for the fixing edge of the holding part to be connected to the edge of the filtration medium by means of a clamping connection.

The disk-shaped filtration medium which is coordinated with the processing device provided is usually of rotationally symmetrical design, though may also have a rectangular structure or some other polygonal structure and also geometrically irregular forms. The corresponding device for holding a filtration medium or the holding part is functionally coordinated, in terms of its encircling contour, with the contour or structure of the disk-shaped filtration medium so as to produce adhesive contact or a clamping connection only in the region which has not been wetted by the medium and the preceding filtration, and which is not used for further analysis.

The adhesion layer is formed from a PSA ("Pressure Sensitive Adhesive") dispersion adhesive or from acrylate copolymer microspheres. In this way, even wet filters can be adequately bonded to the fixing edge of the holding part and if appropriate also removed again. Suitable pressure-sensitive adhesives are known to a person skilled in the art for example as acrylate adhesives based on microspheres. Here, adhesives may be used which can be sterilized using common methods.

Furthermore, adhesives are used which do not exhibit any non-specific reactions or signals with reagents and reaction methods used in the subsequent analytics. In particular, the adhesive is preferably free from DNA and protein and has no elutable components which, by staining, fluorescence or chemical reaction, disrupt the subsequent analytics.

In a further preferred embodiment of the invention, a cover which corresponds to the holding part can be mounted on the holding part with filtration medium held therein, wherein the cover has a cavity which is formed as a reservoir and distributor for flushing liquid. In this way, the holding part can be used as a liquid distributor which serves for the contacting, for the dosing of the spatial distribution and for the uniform discharging of the flushing liquid during the contacting and flushing process. Here, the holding part is formed such that, after the removal of the porous filtration medium with the holding part from a first processing device, said holding part is mounted and fixed on the top side or retentate side of the filtration medium. Here, the cover can close off the underside of the filtration medium such that a reverse contamination of the filtration medium and of the sample volumes during the handling steps is prevented.

In a further preferred embodiment of the invention, the cover has, on the side facing away from the holding part, an orifice which can be repeatedly reclosed by a closure. Different quantities and/or types of flushing or processing liquids can be introduced through the orifice.

In a further preferred embodiment, the cover has further orifices arranged and formed so as to ensure uniform, air-bubble-free filling of the flushing liquid reservoir.

In a further preferred embodiment of the invention, the reservoir is filled with a porous medium. The porous medium serves to absorb and distribute the flushing liquid over the filtration medium. The porous medium of the reservoir may bear areally against the underside of the filtration medium. The cover is formed with its reservoir such that it can absorb and areally distribute a defined volume.

The holding part and the associated cover may be designed such that the filtration medium is sealed off radially toward the edge in the region outside the filtration surface by the cover, and such that outflow ducts and surfaces are provided which are situated below the filtration medium and which are angled so as to slope downward toward the collecting vessel. By means of these and other similar sealing features, it can be ensured that, in the case of centrifugation flushing, all of the flushing medium is conveyed through the filtration medium into the collecting vessel, without remaining in the region laterally outside the filtration medium owing to the centrifugal force, and thus being lost with regard to the further analysis.

The cover may be sterilely packaged and in particular delivered in a state in which it is sterilely closed off at its underside, which faces toward the holding part, by means of a detachable sterile barrier. It is also possible for the cover to be delivered in a state in which it is filled with flushing liquid. Here, the flushing liquid is particularly suitable for releasing adherent particles during the reverse flushing. In particular, the flushing or processing liquid is suitable for releasing the microorganisms adhered to the filtration medium, lysing said microorganisms and/or extracting the components then released.

As a result of the contact of the cover which is filled with processing liquid, it is possible, by means of a corresponding time and temperature profile, to ensure that corresponding reactions with the adherent germs are completed before the reaction products are transferred, by the reverse flushing, into the collecting vessel or into adjoining filtering or adsorption units.

The holding part and the cover are suitable for the corresponding subsequent analytics, and are in particular free from disruptive contaminants. For PCR in particular, DNA-free products are required.

In a further preferred embodiment of the invention, between the outlet of the holding part and the collecting vessel, there are fitted a removable filter and/or a corresponding adsorption unit which permit further processing steps for concentration, purification and elution.

The object with regard to the method is achieved in conjunction with the preamble of Claim 11 in that the holding part with the filtration medium held therein is turned upside down, and that components retained on the filtration medium are reverse-flushed out and collected in a detachably connected collecting vessel.

As a result of the fact that the holding part with the filtration medium held therein is turned upside down, it is not necessary for the filtration medium to be removed from the holding part for the purpose of reverse flushing. The collecting vessel which is connected to the holding part furthermore reliably prevents the possibility of undesired contamination during the mounting of the collecting vessel. The outlay for reverse flushing is thus made considerably simpler and safer.

The device for the processing of the filtration medium may be delivered in sterilely packaged form. Here, the holding part may be closed off at its holding opening, which is arranged on the underside facing away from the outlet, by a sterile closure for example in the form of an adherent foil. The sterile closure projects with a tab laterally beyond the circumference of the holding part.

Before the first use of the device or of the holding part, the sterile closure is gripped by the tab and pulled off the holding part.

In a preferred embodiment of the invention, after the holding part is turned over, a cover having a cavity which forms a reservoir and which has been filled with flushing liquid is mounted onto the holding part and inserted into a further processing device, wherein the liquid is discharged from the reservoir in order to flush out the components.

As a result of the fact that the cover is mounted onto the holding part after the latter is turned over, the holding part with the filtration medium and the cover can be inserted into a further processing station, for example a centrifuge, in a simple and safe manner. Without additional manipulation, it is possible for the filtration medium to be reverse-flushed with liquid from the reservoir, or centrifuged, in the processing station, such that the retained, preferably particulate components are flushed out and collected by the collecting vessel of the holding part.

The cover may likewise be delivered in sterilely packaged form. In particular, the free space, which is formed as a flushing liquid distributor, of the cover may likewise be provided so as to be sterilely closed off in the direction of the holding part by a detachable sterile barrier. The sterile barrier may for example be in the form of an adherent foil.

The sterile barrier projects with a tab laterally beyond the circumference of the cover.

Before the first use of the cover, the sterile barrier is gripped by the tab and pulled off the cover.

Simple and cheap manipulation of the filtration medium with the sample deposited thereon is thus attained.

Further features of the invention will emerge from the following detailed description and from the appended drawings, which illustrate preferred embodiments of the invention by way of example.

DETAILED DESCRIPTION OF THE PREFERRED EMBODIMENTS

Figure 1:
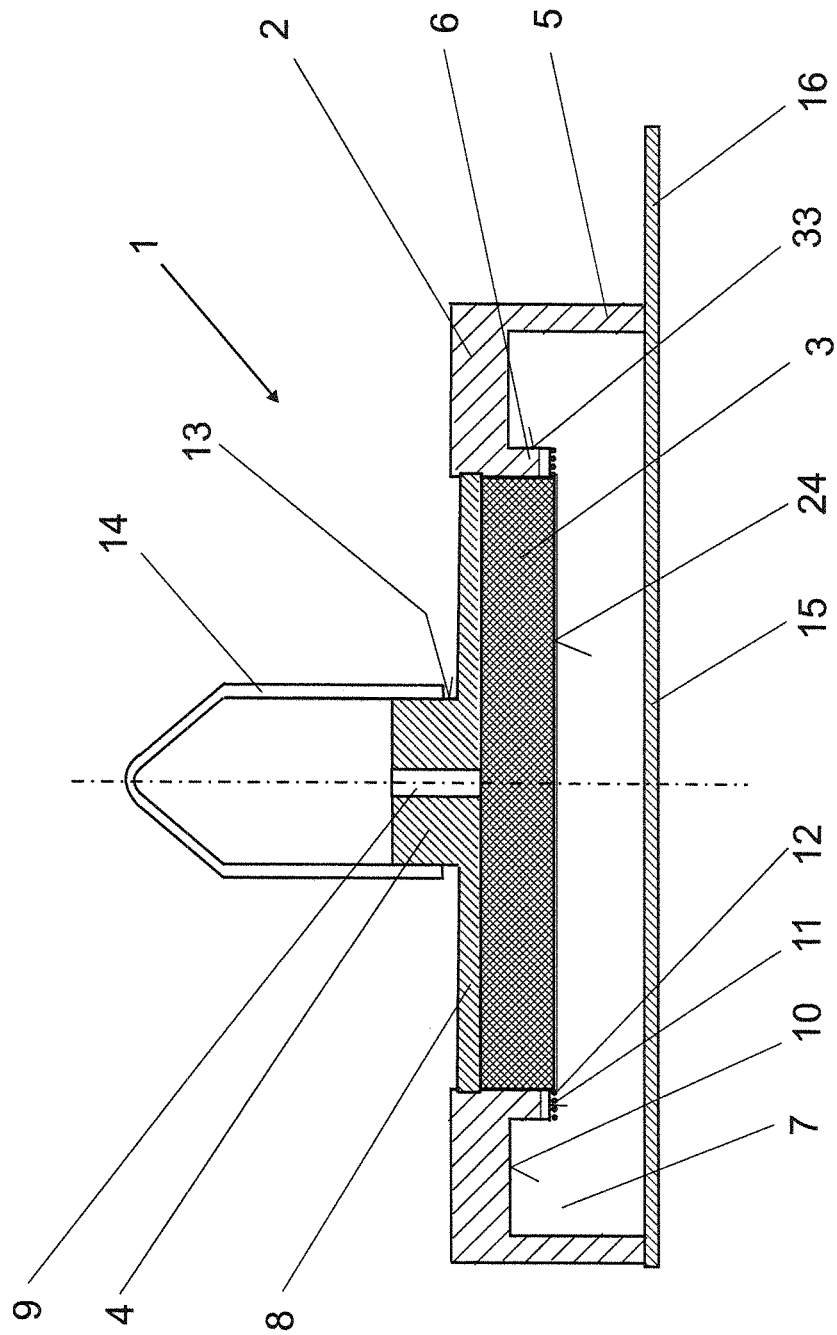
FIG. 1 shows a side view of a device for processing a filtration medium in section, having a holding part with a filtration support, having an outlet with a collecting vessel plugged thereon, and having a sterile closure.

A device 1 is composed substantially of a holding part 2, of a filtration support 3 and of an outlet 4.

The holding part 2 forms an encircling contour with an outer wall 5 and with an inner wall 6 running parallel thereto, said inner wall surrounding a shoulder 7 in the holding part 2, which shoulder is delimited in the upward vertical direction by a top wall 8 which has, in the cylindrical outlet 4 integrally formed thereon, a central orifice 9. The filtration support 3, which is composed of a material permeable to liquid, is arranged in the shoulder 7.

The holding part 2 has, on its holding part inner surface 10 facing away from the top wall 8, the inner wall 6 whose free end forms, with its end surface, a fixing edge 11. In the exemplary embodiments, the fixing edge 11 has an adhesion layer 12 composed of a suitable adhesive.

The adhesion layer 12 is formed for example from a PSA dispersion adhesive or from acrylate copolymer microspheres.

A collecting vessel 14 is plugged onto the lateral surface 13 of the outlet 4. The collecting vessel 14 which is detachably connected to the outlet 4 is formed for example as an Eppendorf vessel known per se or "spin tube".

Corresponding to the exemplary embodiment of FIG. 1, the holding part 2 has, on its free end of the outer wall 5, a sealing sterile closure 15 which can be pulled off the holding part 2 or the outer wall 5 by means of a tab 16.

Figure 2:
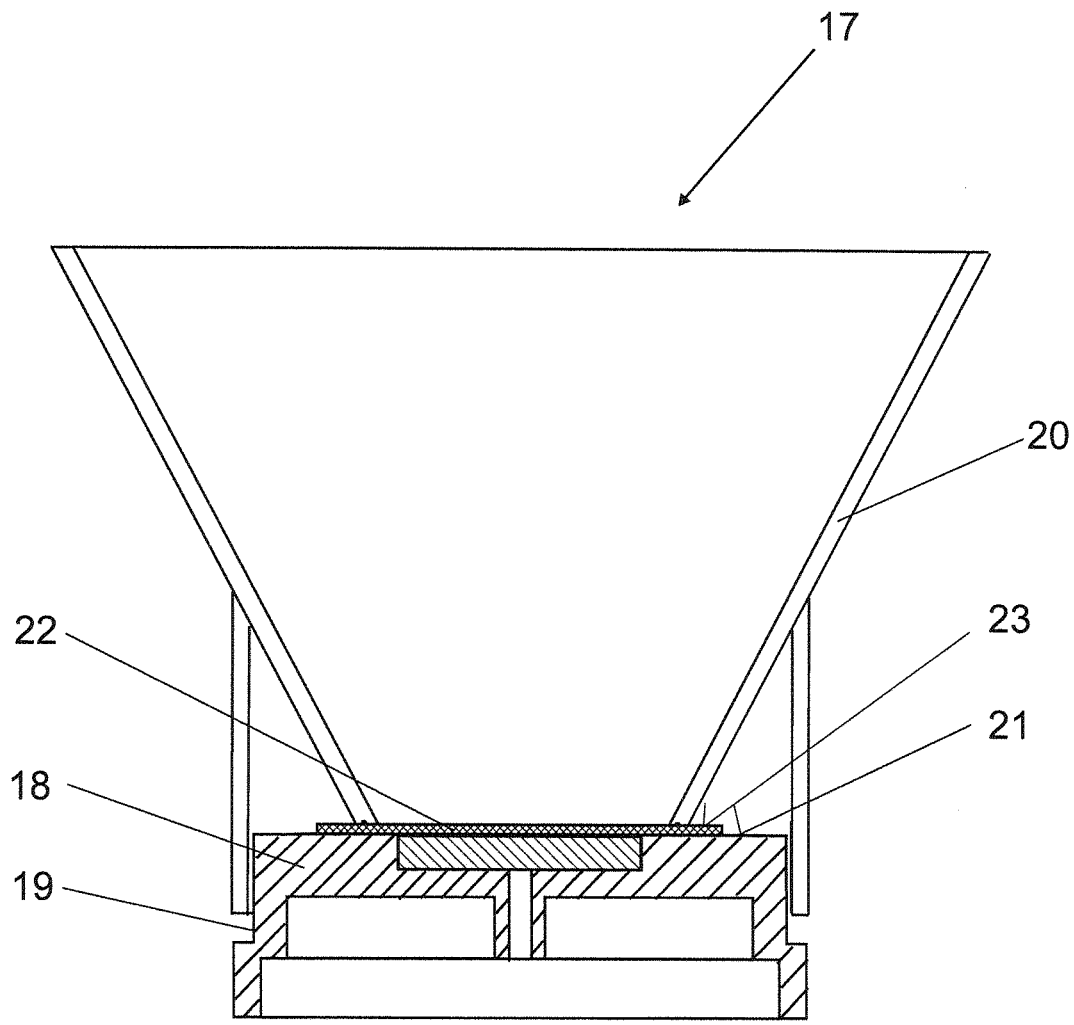
FIG. 2 shows a sectional side view of a first filtration device with a filtration medium arranged on a lower part.

A first processing device known per se, which is formed, correspondingly to FIG. 2, as a filtration device 17, is composed of a lower part 18 with a holding shoulder 19 onto which a funnel-shaped attachment 20 can be mounted. Between the attachment 20 and a filter support surface 21 of the lower part 18 there is arranged a preferably disk-shaped filtration medium 22 formed for example as a porous filter diaphragm.

Figure 3:
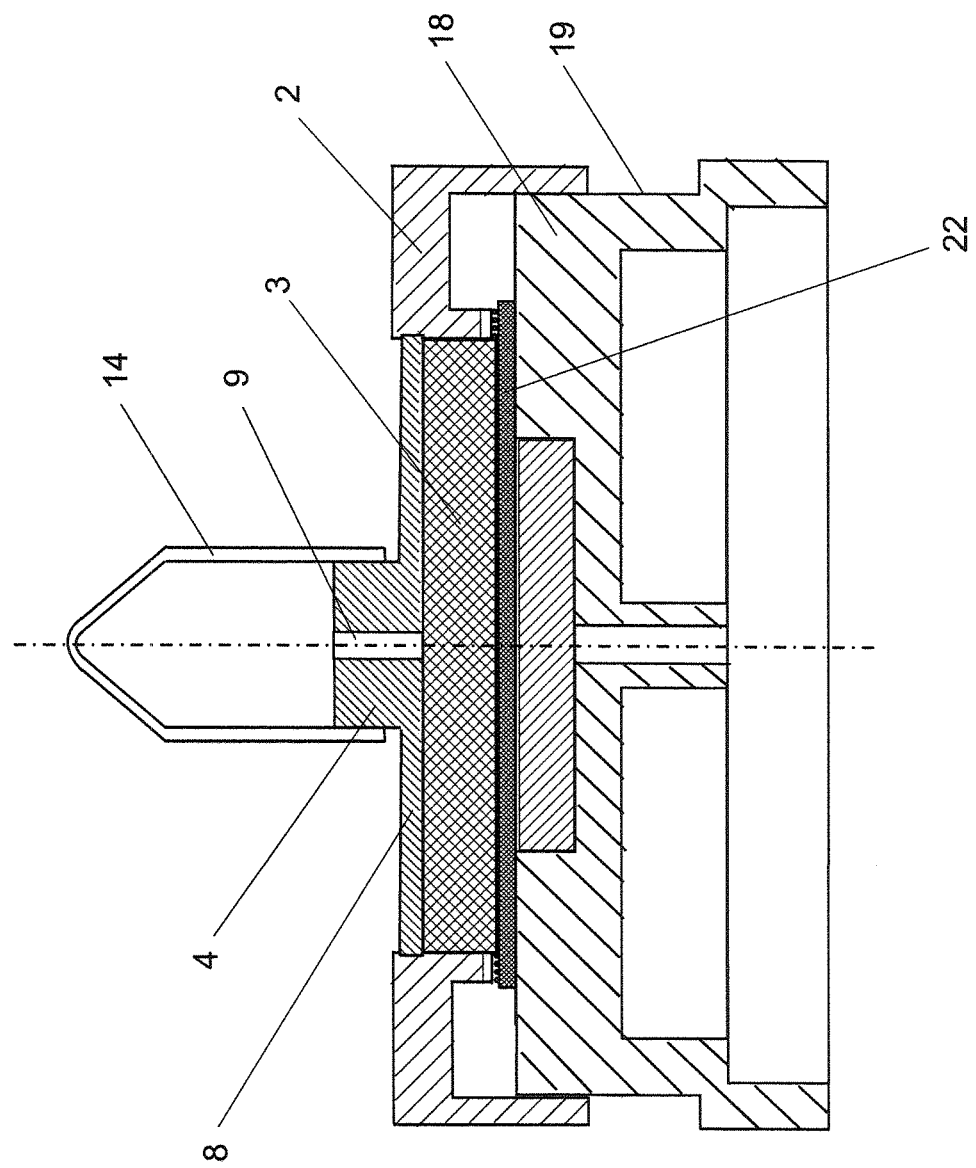
FIG. 3 shows a sectional side view of the holding part from FIG. 1 on the lower part with filtration medium from FIG. 2.

After a filtration process, the attachment 20 can be removed from the lower part 18, and the holding part 2 of the device 1 can, with the collecting vessel 14 plugged thereon, be mounted on the lower part 18 in place of the attachment 20. Here, the holding part 2 is mounted with its fixing edge 11 onto an edge 23 of the disk-shaped filtration medium 22, such that the disk-shaped filtration medium 22 adheres to the adhesive layer 12 of the fixing edge 11 and can be held by the lower part 18 as per FIG. 3.

Figure 4:
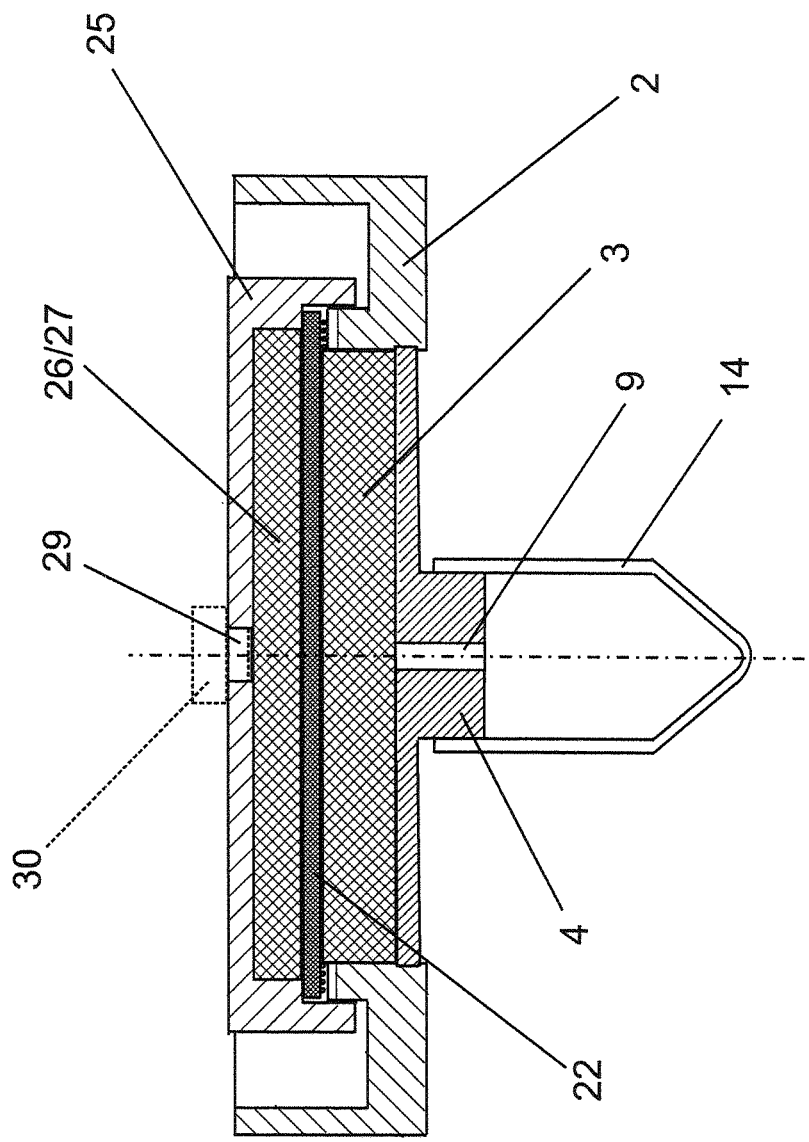
FIG. 4 shows a sectional side view of the holding part of FIG. 1, with filtration medium and mounted cover, turned upside down.
Figure 5:
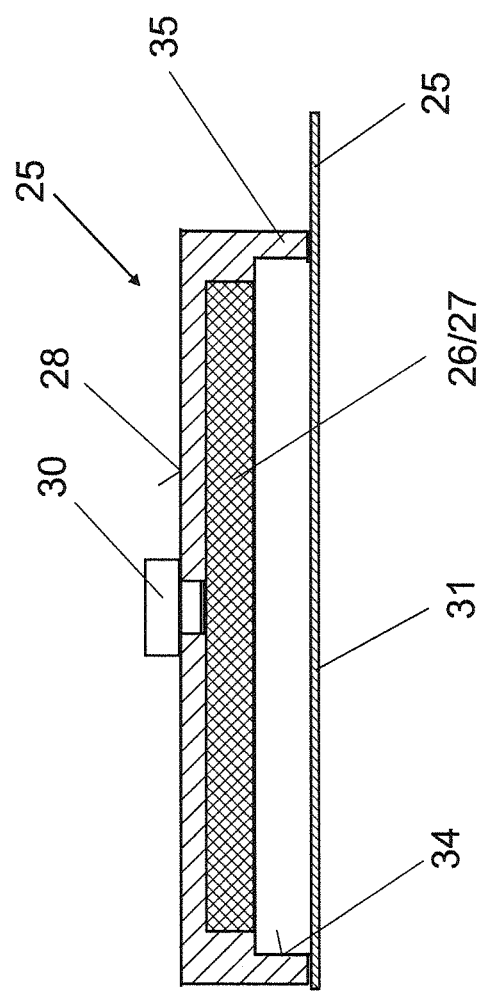
FIG. 5 shows a sectional side view of the cover of FIG. 4 with a sterile barrier.

The device 1 or the holding part 2 can now, with the filtration medium 22, be turned upside down as per FIG. 4, wherein the disk-shaped porous filtration medium 22 rests on the underside 24, which faces away from the top wall 8, of the filtration support.

A cover 25 can be mounted, as per FIG. 4, onto the inner wall 6 of the holding part 2 with the filtration medium 22 in order to close off the device 1 or the holding part 2.

The cover 25 comprises a cavity 26 which serves as a reservoir and distributor for flushing liquid. The cavity 26 is filled with a porous medium 27 which can store flushing liquid and which serves as a distributor.

The dimensions of the cover 25 are such that it, by means of its inner surface 34 of the side wall 35, laterally encompasses the fixing edge 11 of the holding part 2 at the lateral surface 33 of the inner wall 6, and it comes to rest on the filtration medium 22.

The cover 25 has, on its outer side 28 facing away from the holding part 2, a central orifice 29 for flushing stages, which orifice can be closed off by a closure 30. The orifice 29 permits uniform, areal wetting and aeration of the reservoir or cavity 26 in the porous medium 27 thereof, which can be easily saturated with flushing liquid and which also uniformly discharges said flushing liquid again during the flushing process, for example by centrifugation.

For the flushing process, a pressure compensation device, for example an air orifice, must be provided between the collecting vessel 14 and the outlet 4, and between the closure 30 and the cover 25, in order to be able to correspondingly effect the liquid changes.

The flushing process may be carried out under the action of different driving forces, for example by vacuum filtration after the opening of the closure 30 and the sealing mounting of the holding part 2.

Centrifugation is preferable because, by means thereof, it is possible for extremely small volumes to be collected in the collecting vessel 14.

The cover 25 with the cavity 26 formed as a flushing liquid reservoir may also be offered in sterile form with a sterile barrier 31 including opening tab 32 in order to prevent contamination of the sample.

Figure 6:
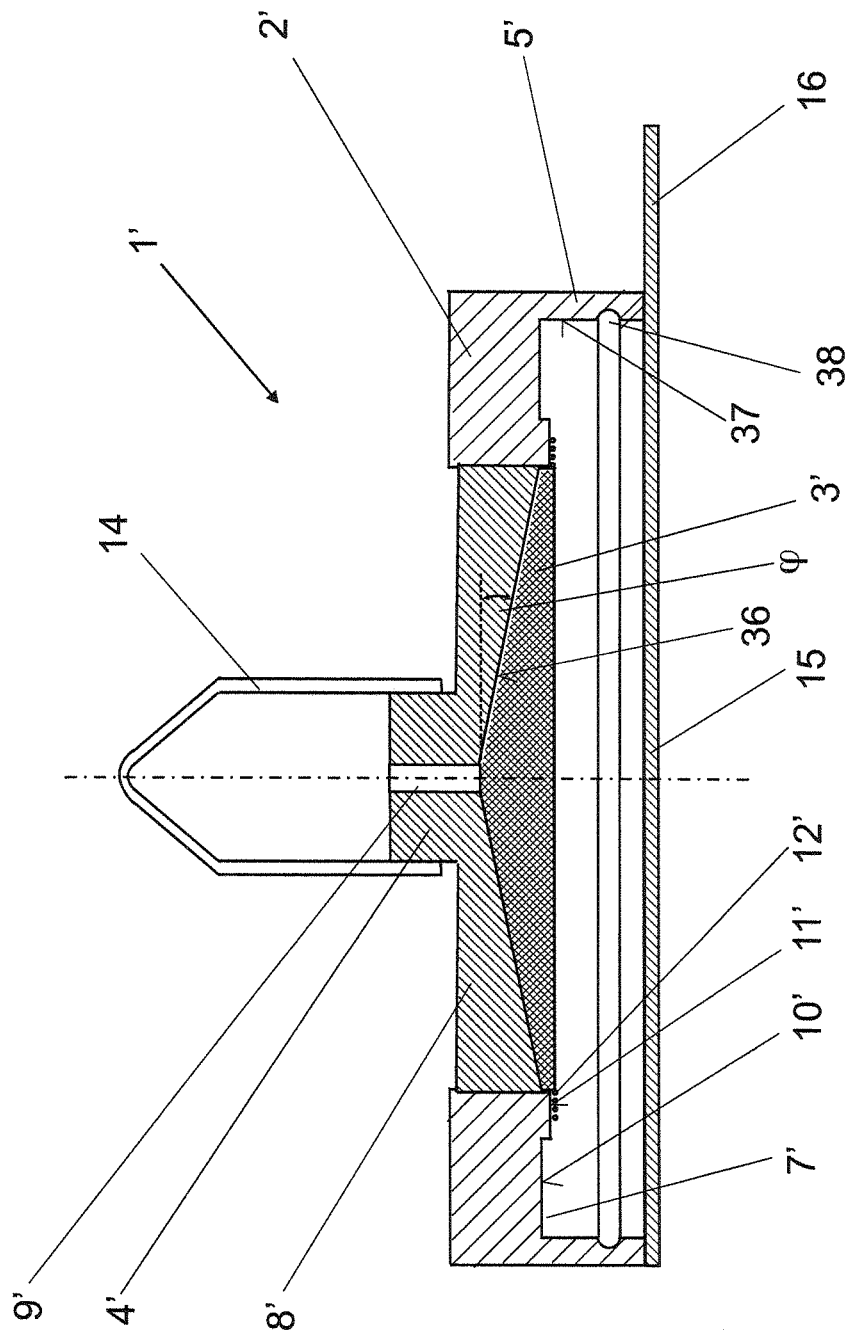
FIG. 6 shows a sectional side view of a further holding part with filtration medium and mounted cover.

FIG. 6 illustrates a device 1' whose holding part 2' with the filtration support 3' is designed especially for a centrifugation application. The holding part 2' forms an encircling contour with an outer wall 5' which surrounds a shoulder 7' in the holding part 2', which shoulder is delimited in the upward vertical direction by a top wall 8' which has, in the cylindrical outlet 4' integrally formed thereon, a central orifice 9'. The filtration support 3', which is composed of a material permeable to liquid, is arranged in the shoulder 7'.

The holding part 2' has, on its holding part inner surface 10' facing away from the top wall 8', a circular fixing edge 11' which surrounds the filtration support 3'. In the exemplary embodiments, the fixing edge 11, 11' has an adhesion layer 12 composed of a suitable adhesive. The top wall 8' is formed such that its inner outflow surface 36 is of frustoconical form, sloping downward at an angle φ with respect to a horizontal toward the collecting vessel 14.

Figure 7:
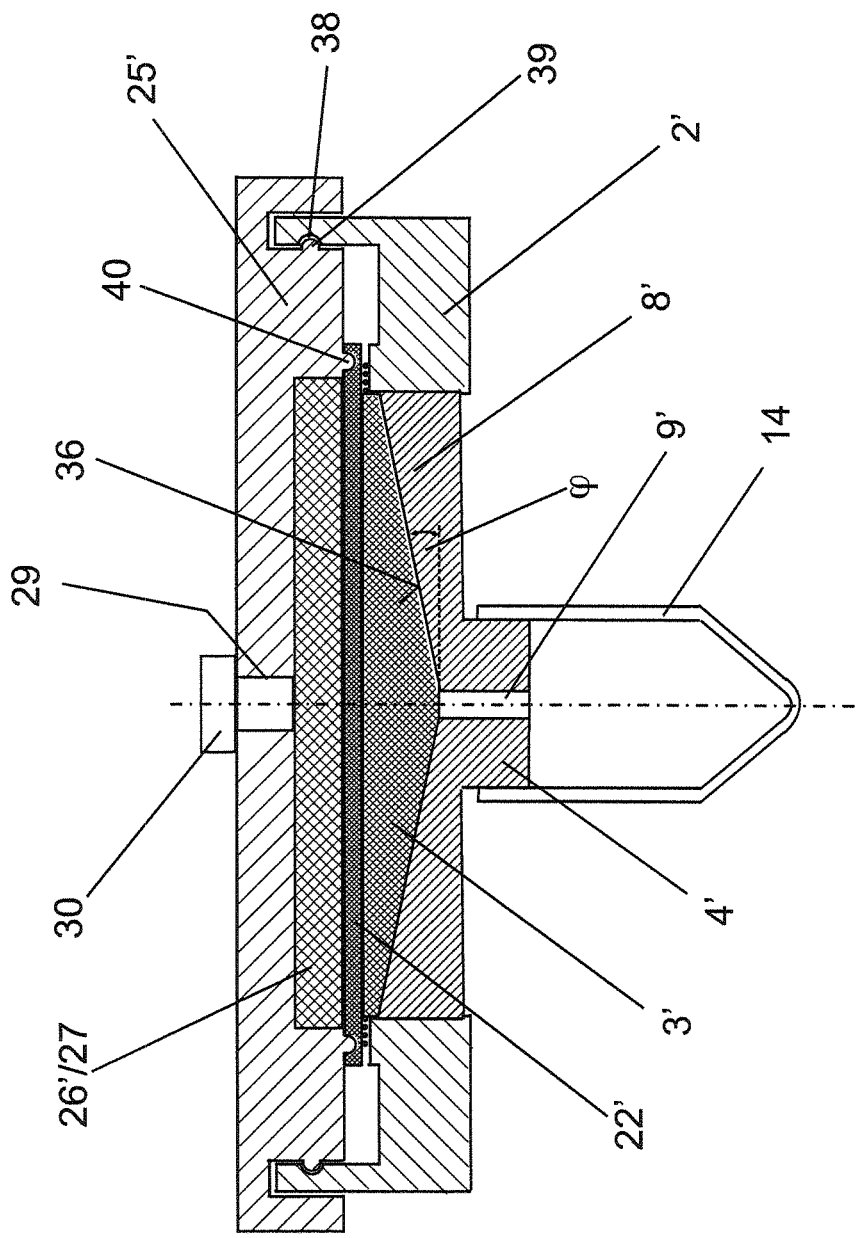
FIG. 7 shows a sectional side view of a further device for processing a filtration medium, composed of a holding part with a filtration support, of an outlet with collecting vessel plugged thereon, and of a sterile closure.

A cover 25' can be mounted into the holding part 2' with the filtration medium 22 in order to close off the device 1' or the holding part 2', as per FIG. 7.

The cover 25' comprises a cavity 26' which serves as a reservoir and distributor for flushing liquid. The cavity 26' is filled with a porous medium 27 which can store flushing liquid and which serves as a distributor.

The dimensions of the cover 25' are such that it completely covers the fixing edge 11' of the holding part 2' and the filtration medium 22', comes to rest on the filtration medium 22' and fills out the interior of the holding part 2'.

The cover 25' has, on its outer side 28' facing away from the holding part 2', a central orifice 29' for flushing stages, which orifice can be closed off by a closure 30'. The orifice 29' permits uniform, areal wetting and aeration of the reservoir or cavity 26' in the porous medium 27 thereof, which can be easily saturated with flushing liquid and which also uniformly discharges said flushing liquid again during the flushing process, for example by centrifugation.

In the inner surface 37 of the outer wall 5' there is arranged an encircling annular depression 38 which corresponds to a bead 39 on the cover 25'. The cover 25' is thereby fixed. The filtration medium 22 is sealed off radially to the outside by means of a sealing edge 40 of the cover 25', in that the sealing edge 40 presses into the filtration medium 22 as per FIG. 7.

By means of these and other similar sealing features, it is ensured that, in the case of centrifugation flushing, all of the flushing medium is conveyed through the filtration medium 22' into the collecting vessel, without remaining in the region laterally outside the filtration medium 22' owing to the centrifugal force, and thus being lost with regard to the further analysis.

The invention claimed is:

1. A device (1, 1') for removing a porous filtration medium (22, 22') from a lower part (18) of a filtration device (17) and enabling a transfer of retained components from the filtration medium (22 22') for collection, the device comprising:
a holding part (2, 2') and a cover (25, 25'), wherein:
the holding part (2, 2') includes:
an outer wall (5, 5') having an inner circumferential surface positionable outside an outer circumferential surface of the lower part (18) that has the filtration medium (22, 22') thereon,
an inner wall (6) having an outer circumferential surface spaced inward from and opposed to the inner circumferential surface of the outer wall (5, 5'), an inner surface opposite the outer circumferential surface and a fixing edge (11, 11') between the outer circumferential surface and the inner surface, the fixing edge (11, 11') being positionable on and engageable with an edge (23) of the filtration medium (22, 22') for separating the filtration medium (22, 22') from the lower part (18),
a filtration support (3) inward of the inner surface of the inner wall (6) and supporting the filtration medium (22, 22'), and
an outlet (4) communicating with a side of the filtration support (3) facing away from the filtration medium (22, 22') for reverse flushing; and
the cover (25, 25') is configured for mounting to the outer circumferential surface of the inner wall (6) of the holding part (2, 2') at a position opposed to the filtration medium (22, 22'), the cover (25, 25') having a cavity (26, 26') communicating with a side of the filtration medium (22, 22') opposite the outlet (4) and defining a reservoir and distributor for flushing a liquid through the filtration medium (22, 22') and transferring the retained components from the filtration medium (22 22') to the outlet (4).

2. The device of claim 1, further comprising:
a porous medium (27) in the cavity (26, 26') of the cover (25, 25') and opposed to the filtration medium (22) for storing the flushing liquid and distributing the flushing liquid to the filtration medium (22).

3. The device of claim 1, further comprising:
a detachable collecting vessel (14) connected to the outlet (4).

4. The device of claim 1,
wherein the fixing edge (11, 11') of the holding part (2, 2') can be connected to the edge (23) of the filtration medium (22, 22') by an adhesive bond.

5. The device of claim 1,
wherein the fixing edge (11, 11') of the holding part (2) can be connected to the edge (23) of the filtration medium (22, 22') by a clamping connection.

6. The device of claim 1,
wherein the fixing edge (11, 11') of the holding part (2, 2') or the edge (23) of the filtration medium (22, 22') has an adhesion layer (12) composed of an adhesive that is engageable with the filtration medium (22, 22').

7. The device of claim 1,
wherein the cover (25, 25') has, on its side facing away from the holding part (2, 2'), an orifice (29) that can be closed off by a closure (30).

8. The device of claim 1,
wherein, between the outlet (4, 4') and the collecting vessel (14), there are fitted a removable filter and a corresponding adsorption unit which permit further processing steps for concentration, purification and elution.

9. The device of claim 1,
wherein the lower part (18) and the holding part (2, 2') are disposable articles.

10. A method for processing a porous filtration medium (22, 22') that is arranged in a lower part (18) of a filtration device (17) and that is exposed to a liquid sample, the method comprising:

mounting an inner circumferential surface of an outer wall (5, 5') of a holding part (2, 2') of a device (1, 1') on and around the lower part (18) of the filtration device (17);

connecting a fixing edge (11, 11') of an inner wall (6, 6') that is spaced inward of the outer wall (5, 5') of the holding part (2, 2') to an edge (23) of the filtration medium (22, 22');

raising the holding part, together with the filtration medium (22, 22') connected thereto, from the lower part (18);

turning the holding part (2, 2') with the filtration medium (22, 22') held therein upside down;

mounting a cover (25, 25') to the inner wall (6, 6') of the holding part (2, 2') that has been turned over so that a cavity (26, 26') of the cover (25, 25') is opposed to the filtration medium (22, 22'); and filling the cavity (26, 26') with a flushing liquid for reverse flushing-out and collecting components retained on the filtration medium (22, 22') in a detachably connected collecting vessel (14).

* * * * *